US008846059B2

(12) United States Patent
Suckow et al.

(10) Patent No.: US 8,846,059 B2
(45) Date of Patent: *Sep. 30, 2014

(54) EXTRACELLULAR MATRIX ADJUVANT AND METHODS FOR PREVENTION AND/OR INHIBITION OF OVARIAN TUMORS AND OVARIAN CANCER

(75) Inventors: Mark A. Suckow, Granger, IN (US); William Wolter, Granger, IN (US)

(73) Assignee: University of Notre Dame, Notre Dame, IN (US)

( * ) Notice: Subject to any disclaimer, the term of this patent is extended or adjusted under 35 U.S.C. 154(b) by 420 days.

This patent is subject to a terminal disclaimer.

(21) Appl. No.: 12/633,152

(22) Filed: Dec. 8, 2009

(65) Prior Publication Data

US 2011/0135690 A1    Jun. 9, 2011

(51) Int. Cl.
*A61K 9/00* (2006.01)
*A61K 9/14* (2006.01)
*A61K 9/70* (2006.01)
*A61K 39/00* (2006.01)

(52) U.S. Cl.
CPC ... *A61K 39/0011* (2013.01); *A61K 2039/55588* (2013.01)
USPC ........ 424/277.1; 424/423; 424/443; 424/484; 424/489

(58) Field of Classification Search
None
See application file for complete search history.

(56) References Cited

U.S. PATENT DOCUMENTS

| | | | |
|---|---|---|---|
| 2,172,903 A | 9/1939 | Charping |
| 3,346,401 A | 10/1967 | Barat et al. |
| 3,562,820 A | 2/1971 | Braun |
| 3,810,473 A | 5/1974 | Cruz, Jr. et al. |
| 4,502,159 A | 3/1985 | Woodroof et al. |
| 4,578,067 A | 3/1986 | Cruz, Jr. et al. |
| 4,902,508 A | 2/1990 | Badylak et al. |
| 4,956,178 A | 9/1990 | Badylak et al. |
| 5,028,695 A | 7/1991 | Eckmayer et al. |
| 5,275,826 A | 1/1994 | Badylak et al. |
| 5,281,422 A | 1/1994 | Badylak et al. |
| 5,336,616 A | 8/1994 | Livesey et al. |
| 5,352,463 A | 10/1994 | Badylak et al. |
| 5,372,821 A | 12/1994 | Badylak et al. |
| 5,437,287 A | 8/1995 | Phillips et al. |
| 5,460,962 A | 10/1995 | Kemp |
| 5,480,424 A | 1/1996 | Cox |
| 5,507,810 A | 4/1996 | Prewett et al. |
| 5,554,389 A | 9/1996 | Badylak et al. |
| 5,695,998 A | 12/1997 | Badylak et al. |
| 5,733,337 A | 3/1998 | Carr, Jr. et al. |
| 5,782,914 A | 7/1998 | Schankereli |
| 5,837,269 A | 11/1998 | Daynes et al. |
| 6,120,991 A | 9/2000 | Carter et al. |
| 6,156,305 A | 12/2000 | Brauker et al. |
| 6,206,931 B1 | 3/2001 | Cook et al. |
| 6,207,147 B1 | 3/2001 | Hiserodt et al. |
| 6,218,166 B1 | 4/2001 | Ravindranath et al. |
| 6,264,992 B1 | 7/2001 | Voytik-Harbin et al. |
| 6,277,368 B1 | 8/2001 | Hiserodt et al. |
| 6,403,104 B1 | 6/2002 | Berd et al. |
| 6,406,689 B1 | 6/2002 | Falkenberg et al. |
| 6,451,971 B1 | 9/2002 | Akiyama et al. |
| 6,548,066 B1 | 4/2003 | Michaeli et al. |
| 6,699,483 B1 | 3/2004 | Dalgleish et al. |
| 7,015,205 B1 | 3/2006 | Wallack et al. |
| 7,090,853 B2 | 8/2006 | Kapp et al. |
| 7,175,652 B2 | 2/2007 | Cook et al. |
| 7,550,004 B2 | 6/2009 | Bahler et al. |
| 2001/0006631 A1 | 7/2001 | Hiserodt et al. |
| 2002/0001595 A1 | 1/2002 | Sonntag et al. |
| 2004/0013712 A1 | 1/2004 | Parma |
| 2006/0099675 A1 | 5/2006 | Benard |
| 2006/0265053 A1 | 11/2006 | Hunt |
| 2007/0128174 A1 | 6/2007 | Kleinsek et al. |
| 2008/0107665 A1 | 5/2008 | Suckow et al. |
| 2008/0160049 A1 | 7/2008 | Suckow et al. |
| 2008/0260800 A1 | 10/2008 | Suckow et al. |
| 2009/0220461 A1 | 9/2009 | Suckow et al. |
| 2009/0248144 A1 | 10/2009 | Bahler et al. |

FOREIGN PATENT DOCUMENTS

| | | |
|---|---|---|
| WO | WO97/36495 | 10/1997 |
| WO | WO 00/09140 | * 2/2000 |
| WO | WO03/100034 | 12/2003 |
| WO | WO2006/110827 | * 10/2006 |
| WO | WO 2007/035843 | * 3/2007 |
| WO | WO2008/051852 | 5/2008 |
| WO | WO2008/094276 | 8/2008 |
| WO | WO2008/112344 | 9/2008 |
| WO | WO2009/108656 | 9/2008 |

OTHER PUBLICATIONS

DeVita et al (Cancer, Principles and Practice of Oncology, 5th Ed., 1997, p. 1504).*
Suckow et al (Journal of Materials Science. Materials in Medicine, 2007, vol. 18, pp. 1105-1110).*
Wheeler (Salud p'ublica de M'exico, 1997, vol. 39, pp. 283-287).*
Efferson et al (Anticancer research, 2005, vol. 25, pp. 715-724).*
Bachman et al (Journal of Immunology, 2005, vol. 175, pp. 4677-4685).*
Stewart et al (Cancer Research, 2004, vol. 64, pp. 8177-8183).*
Abraham et al., (2000), "Evaluation of the Porcine Intestinal Collagen Layer as a Biomaterial," J. Biomed. Res., 29:442-452.
Aguzzi et al., (2003), "Immune system and peripheral nerves in propagation of prions to CNS," Br Med Bull., 2003;66:141-59.
Aguzzi et al., (2006), "Pathogenesis of prion diseases: current status and future outlook," Microbiology, 4:765-775.
Akhurst, (2002), "TGF-B antagonists: why suppress a tumor suppressor?" J. Clin. Invest., 109:1533-1536.

(Continued)

*Primary Examiner* — Karen Canella
(74) *Attorney, Agent, or Firm* — Husch Blackwell LLP; Denise L. Mayfield

(57) ABSTRACT

Compositions suitable for use as ovarian cancer and/or tumor adjuvants in the preparation of ovarian cancer vaccines, particularly those vaccines useful in the treatment of human ovarian cancer, are provided. The ovarian cancer adjuvants described are comprised of an extracellular matrix material, such as small intestinal submucosal (SIS) tissue. The preparations may take the form of sheets, gels, liquids (injectable), tracer, or other solid or semi-solid preparation. Also disclosed are ovarian tumor inhibiting compositions that include extracellular matrix tissue adjuvants.

14 Claims, 1 Drawing Sheet

(56) References Cited

OTHER PUBLICATIONS

Allman et al., (2001), "Xenogeneic extracellular matrix grafts elicit a TH2-restricted immune response," Transplantation, 71:1631-1640.
Arbel et al., (2003), "Generation of antibodies against prion protein in wild-type mice via helix 1 peptide immunization," J Neuroimmunol., 144(1-2):38-45.
Baars et al., (2000), "Skin tests predict survival after autologous tumor cell vaccination in metastatic melanoma: experience in 81 patients," Ann. Oncol., 11:965-970.
Badylak et al., (1989), "Small intestinal submucosa as a large diameter vascular graft in the dog," J. Surgical Res., 47:74-80.
Badylak et al., (1998), "Small intestinal submucosa: a substrate for in vitro cell growth," J. Biomater. Sci. Polymer Edn., 9:863-878.
Badylak et al., (2002), "The extracellular matrix as a scaffold for tissue reconstruction," Cell Devel. Biol., 13:377-383.
Badylak, (1993), "Small intestinal submucosa (SIS): a biomaterial conducive to smart tissue remodeling," Tissue Engineering: Current Perspectives, Bell (ed)., Birkhauser Publishers, Cambridge, MA, pp. 179-189.
Banzhoff et al., (2003), "A new MF59-adjuvanted influenza vaccine enhances the immune response in the elderly with chronic diseases: results from an immunogenicity meta-analysis," Gerontology, 49(3):177-84.
Barr et al., (2006), "Co-stimulatory agonists as immunological adjuvants," Vaccine, 24:3399-3407.
Bello-DeOcampo et al., (2004), "TGF-B/Smad signaling in prostate cancer," Curr. Drug Targets, 4:197-207.
Benbow, (2001), "Oasis®: an innovative alternative dressing for chronic wounds," Brit. J. Nursing, 10:1489-1492.
Bendani et al., (2006), "Combined vaccination with idiotype-pulsed allogeneic dendritic cells and soluble protein idiotype for multiple myeloma patients relapsing after reduced-intensity conditioning allogeneic stem cell transplantation," Leukemia & Lymphoma, 41:29-37.
Ben-Efraim et al., (2000), "Use of xenogenized (modified) tumor cells for treatment in experimental tumor and in human neoplasia," Biomed & Pharmacotherapy, 54:268-273.
Berd et al., (1990), "Treatment of metastatic melanoma with an autologous tumor-cell vaccine: clinical and immunologic results in 64 patients," J. Clin. Oncol., 8:8158-1867.
Berd et al., (1997), "Autologous hapten-modified melanoma vaccine as post-surgical adjuvant after resection of nodal metastases," J. Clin. Oncol., 15:2359-2370.
Bergman et al., (2003), "Long-term survival of dogs with advanced malignant melanoma after DNA vaccination with xenogeneic human tyrosinase: a phase I trial," Clin. Cancer Res., 9:1284-1290.
Berraondo et al., (2007), "Eradication of large tumors in mice by a tritherapy targeting the innate, adaptive, and regulatory components of the immune system," Cancer Res., 67:8847-8855.
Bissell et al., (1987), "The influence of extracellular matrix on gene expression: is structure the message?" J. Cell Sci., Suppl 8:327-343.
Bodey et al., (2000), "Failure of cancer vaccines: the significant limitations of this approach to immunotherapy," Anticancer Res., 20:2665-2676.
Boring et al., (1993), "Cancer Statistics," CA Cancer Journal for Clinicians, 43:7-26.
Brando et al., (2007), "Murine immune responses to liver-stage antigen 1 protein FMP011, a malaria vaccine candidate, delivered with adjuvant AS01B or AS02A," Infect Immun., 75(2):838-45.
Brewer, (2006), "(How) do aluminium adjuvants work?" Immunol Lett., 102:10-15.
Brooks et al., (2001), "Plasma selenium level before diagnosis and the risk of prostate cancer development," Journal of Urology, 166:2034-2038.
Brown-Etris et al., (2002), "Part I: A new biomaterial derived from small intestine submucosa and developed into a wound-matrix device," Wounds, 14:150-166.
Burch et al., (2000), "Priming tissue-specific cellular immunity in a phase I trial of autologous dendritic cells for prostate cancer," Clin. Cancer Res., 6:2175-2182.
Burch et al., (2004), "Immunotherapy (APC8015, Provenge) targeting prostatic acid phosphatase can induce durable remission of metastatic androgen-independent prostate cancer: a phase 2 trial," Prostate, 60:197-204.
Caglar et al., (2005), "Effect of monophosphoryl lipid A on antibody response to diphtheria toxin and its subunits," APMIS, 113(4):256-63.
Caughey et al., (2006), "Prions and their Partners in Crime," Nature, 443:803-810.
Chang et al., (2000), "Antigen-Specific Cancer Immunotherapy Using a GM-CSF secreting allogeneic tumor cell-based vaccine," Int. J. Cancer, 86:725-730.
Charles et al., (2000), "Antitumor efficacy of tumor-antigen-encoding recombinant poxvirus immunization in dunning rate prostate cancer: implications for clinical genetic vaccine development," World J. Urol., 18:136-142.
Chatterjee et al., (1994), "Idiotypic antibody immunotherapy of cancer," Cancer Immunol Immunother., 38:75-82.
Corman et al., (1998), "Recognition of prostate-specific antigenic peptide determinants by human CD4 and CD8 T cells," Clin. Exp. Immunol., 114:166-172.
Correale et al., (1997), "In vitro generation of human cytotoxic T lymphocytes specific for peptides derived from prostate-specific antigen," J. Natl. Cancer Inst. USA, 89:293-300.
Culora et al., (1996), "Aluminium and injection site reactions," J. Clin. Pathol., 49:844-847.
Cunha et al., (2003), "Role of the stromal microenvironment in carcinogenesis of the prostate," Int. J. Cancer, 107:1-10.
de Souza Matos et al., (2000), "Immunostimulatory effects of polar glycopeptidolipids of *Mycobacterium chelonae* for inactivated rabies vaccine," Vaccine, 18(20):2125-31.
Degruijl et al., (1999), "Cancer vaccine strategies get bigger and bigger," Nature Medicine, 5:1124-1125.
Denmeade et al., (2003), "Prostate specific antigen (PSA) does not affect growth of prostate cancer cells in vitro or prostate cancer xenografts in vivo," Prostate, 56:45-53.
Desai et al., (2000), "Immune response with biodegradable nanospheres and alum: studies in rabbits using staphylococcal enterotoxin B-toxoid," J Microencapsul., 17(2):215-25.
Dillman et al., (1998), "Clinical experience with autologous tumor cell lines for patient-specific vaccine therapy in metastatic melanoma," Cancer Biother. Radiopharm., 13:165-173.
Dillman et al., (2001), "Short-term cell lines from breast cancer for use as autologous tumor cell vaccines in the treatment of breast cancer," Cancer Biotherapy & Radiopharmaceuticals, 16:205-211.
Dols et al., (2003), "Vaccination of women with metastatic breast cancer using a costimulatory gene (CD80)-modified, HLA-A2 matched allogeneic, breast cancer cell line: clinical and immunological results," Human Gene Therapy, 14:1117-1123.
Donnelly, (2003), "Cancer vaccine targets leukemia," Nature Medicine, 9:1354-1356.
Eaton et al., (2002), "Allogeneic whole-cell vaccine: a phase I/II study in men with hormone-refractory prostate cancer," British Journal of Urology, 89:19-26.
Edwards et al., (2005), "Annual report to the nation on the status of cancer, 1975-2002, featuring population-based trends in cancer treatment," J. Natl. Cancer Inst., 97:1407-27.
Eldridge et al., (1991), "Biodegradable and biocompatible poly(DL-lactide-co-glycolide) microspheres as an adjuvant for staphylococcal enterotoxin B toxoid which enhances the level of toxin-neutralizing antibodies," Infect Immun., 59(9):2978-86.
Enari et al., (2001), "Scrapie prion protein accumulation by scrapie-infected neuroblastoma cells abrogated by exposure to a prion protein antibody," Proc Natl Acad Sci U S A, 98(16):9295-9.
Evans et al., (1999), "Vaccine therapy for cancer—fact or fiction?" Q. J. Med., 92:299-307.
Ezzell, (1995), "Cancer 'vaccines': an idea whose time has come?" J. NIH Res., 7:4-49.
Fernandez-Acenero et al., (2002), "Prognostic influence of tumor-associate eosinophilic infiltrate in colorectal carcinoma," Cancer, 88:1544-1548.
Finn et al., (2002), "Prophylactic Cancer Vaccines," Curr. Opin. Immunol, 14:172-177.

(56) References Cited

OTHER PUBLICATIONS

Flick-Smith et al., (2002), "Mucosal or parenteral administration of microsphere-associated *Bacillus anthracis* protective antigen protects against anthrax infection in mice," Infect Immun., 70(4):2022-8.

Fong et al., (2001), "Dendritic cell-based xenoantigen vaccination for prostate cancer immunotherapy," J. Immunol., 167:7150-7156.

Forni et al., (2000), "Immunoprevention of cancer," Cancer Res., 60:2571-2575.

Frost et al., (1975), "Tumor immunoprophylaxis in mice using glutaraldehyde-treated syngenic tumor cells," Cancer Res., 35:2646-2650.

Fuessel et al., (2006), "Vaccination with hormone-refractory prostate cancer patients with peptide cocktail-loaded dendritic cells: results of phase I clinical trial," Prostate, 66:811-821.

Fukino et al., (2004), "Combined total genome loss of heterozygosity scan of breast cancer stroma and epithelium reveals multiplicity of stromal targets," Cancer Res., 64:7231-6.

Furbert-Harris et al., (2003), "Inhibition of prostate cancer cell growth by activate eosinophils," The Prostate, 57:165-175.

Gann et al., (1999), "Lower prostate cancer risk in men with elevated plasma lycopene levels: results of a prospective analysis," Cancer Research, 59:1225-1230.

Gann et al., (1999), "Lower prostate cancer risk in men with elevated plasma lycopene levels: results of a prospective analysis," JAMA, 281:1682.

Gilch et al., (2003), "Polyclonal anti-PrP auto-antibodies induced with dimeric PrP interfere efficiently with PrPSc propagation in prion-infected cells," J Biol Chem., 278(20):18524-31.

Glenn et al., (2006), "Mass vaccination: solutions in the skin," Curr. Topics Microbiol. Immunol., 304:247-268.

Granziero et al., (1999), "Adoptive immunotherapy prevents prostate cancer in a transgenic animal model," Eur. J. Immunol., 29:1127-1138.

Greenlee et al., (2001), "Cancer Statistics 2001," CA Cancer J. Clin., 51:15-36.

Griffith et al., (2001), "Inhibition of murine prostate tumor growth and activation of immunoregulatory cells with recombinant canarypox viruses," J. Natl. Cancer Inst., 93:998-1007.

Griffiths et al., (1997), "Liposomally-encapsulated ricin toxoid vaccine delivered intratracheally elicits a good immune response and protects against a lethal pulmonary dose of ricin toxin," Vaccine, 15(17-18):1933-9.

Gu et al., (2002), "Substitution of porcine small intestinal submucosa for rabbit Achilles tendon, an experimental study," Natl. Med. J. China, 82:1279-1282 (Chinese language with English abstract).

Gulley et al., (2002), "Phase I study of a vaccine using recombinant vaccinia virus expressing PAS (rV-PSA) in patients with metastatic androgen-independent prostate cancer," The Prostate, 53:109-117.

Hahn et al., (2006), "Short-term dietary administration of celecoxib enhances the efficacy of tumor lysate-pulsed dendritic cell vaccines in treating murine breast cancer," Int. J. Cancer, 118:2220-2231.

Hanan et al., (2001), "Antiaggregating antibody raised against human PrP 106-126 recognizes pathological and normal isoforms of the whole prion protein," Cell Mol Neurobiol., 21(6):693-703.

Hanan et al., (2001), "Immunomodulation of the human prion peptide 106-126 aggregation," Biochem Biophys Res Commun., 280(1):115-20.

Harada et al., (2003), "Prostate-specific antigen-derived epitopes capable of inducing cellular humoral responses in HLA-A24+ prostate cancer patients," Prostate, 57:152-159.

He et al., (2003), "Inhibition of tumor growth with a vaccine based on xenogeneic homologous fibroblast growth factor receptor-1 in mice," J. Biol. Chem., 24:21831-21836.

He et al., (2005), "Antigen epitope-expressing cytokines for DNA immunization," Vaccine, 23:1966-1972.

Hedlund et al., (2001), "Negligible adjuvant effect for antibody responses and frequent adverse events associated with IL-12 treatment in humans vaccinated with pneumococcal polysaccharide," Vaccine, 20(1-2):164-9.

Higaki et al., (2004), "Collagen minipellet as a controlled release delivery system for tetanus and diphtheria toxoid," Vaccine, 19:3091-3096.

Higgins et al., (1996), "MF59 adjuvant enhances the immunogenicity of influenza vaccine in both young and old mice," Vaccine, 14(6):478-84.

Hodde et al., (2002), "Virus safety of a porcine-derived medical device: evaluation of a viral inactivation method," Biotechnol. Bioeng., 79:211-216.

Hodde et al., (2004), "Small Intestinal Submucosa does not promote PAIII tumor growth in Lobund-Wistar rats," J. Surg. Res., 120:189-194.

Hodge et al., (2006), "Costimulatory molecules as adjuvants for immunotherapy," Front. Biosci., 11:788-803.

Horiguchi et al., (2002), "Screening of HLA-A24-restricted epitope peptides from prostate-specific membrane antigen that induces specific antitumor cytotoxic T lymphocytes," Clin. Cancer Res., 8:3885-3892.

Hrouda et al, (1998), "*Mycobacterium vaccae* (SRL172): a potential immunological adjuvant elevated in rate prostate cancer," 82:870-876.

Hrouda et al., (2000), "Allogeneic whole-tumor cell vaccination in the rat model of prostate cancer," BJU International, 86:742-748.

Huang et al., (2005), "A differential proteome in tumors suppressed by an adenovirus-based skin patch vaccine encoding human carcinoembryonic antigen," Proteomics, 5:1013-1023.

Hursting et al., (1990), "Types of dietary fat and the incidence of cancer at five sites," Preventive Medicine, 19:242-253.

Jaganathan et al., (2006), "Strong systemic and mucosal immune responses to surface-modified PLGA microspheres containing recombinant hepatitis B antigen administered intranasally," Vaccine, 24(19):4201-11.

Jager et al., (2003), "Antigen-specific immunotherapy and cancer vaccines," Intl. J. Cancer, 106:817-820.

Jarvinen et al., (2000), "Intranasal vaccination of New Zealand white rabbits against pasteurellosis using alginate-encapsulated *Pasteurella multocida* toxin and potassium thiocyanate extract," Comparative Medicine, 50:263-269.

Jocham et al., (2004), "Adjuvant autologous renal tumour cell vaccine and risk of tumour progression in patients with renal-cell carcinoma after radical neprectomy: phase III, randomised controlled trial," Lancet, 363:594-599.
Kende et al., (2006), "Enhancement of intranasal vaccination in mice with deglycosylated chain A ricin by LTR72, a novel mucosal adjuvant," Vaccine, 15;24(12):2213-21.
Kenney et al., (1999), "Protective immunity using recombinant human IL-12 and alum as adjuvants in a primate model of cutaneous leishmaniasis," J Immunol., 163(8):4481-8.
Kenney et al., (2004), "Induction of protective immunity against lethal anthrax challenge with a patch," J. Infect. Disease, 190:774-782.
Knoll, (2001), "Use of porcine small intestinal submucosal graft in the surgical management of personae's disease," Urology, 57:753-757.
Knoll, (2002), "Use of porcine small intestinal submucosal graft in the surgical management of tunical deficiencies with penile prosthetic surgery," Urology, 59:758-761.
Kobayashi et al., (2003), "Identification of naturally processed helper T-cell epitopes from prostate-specific membrane antigen using peptide-based in vitro stimulation," Clin. Cancer Res., 9:5386-5393.
Kochenderfer et al., (2007), "Maximizing CD8+ T cell responses elicited by peptide vaccines containing CpG oligodeoxynucleotides," Clin. Immunol., 124:119-130.
Koller et al., (2002), "Induction of antibodies against murine full-length prion protein in wild-type mice," J Neuroimmunol., 132(1-2):113-6.
Komenaka et al., (2004), "Immunotherapy for melanoma," Clinics in Dermatology, 22:251-265.
Langermans et al., (2005), "Effect of adjuvant on reactogenicity and long-term immunogenicity of the malaria Vaccine ICC-1132 in macaques," Vaccine, 23(41):4935-43.
Lantz et al., (1990), "Small intestinal submucosa as a small-diameter arterial graft in the dog," J. Invest. Surg., 3:217-227.

(56) References Cited

OTHER PUBLICATIONS

Lantz et al., (1993), "Small intestinal submucosa as a vascular graft: a review," J. Invest. Surg., 6:297-310.

Lee et al., (1999), "Increased vaccine-specific T cell frequency after peptide-based vaccination correlates with increased susceptibility to in vitro stimulation but does not lead to tumor regression," J. Immunol., 163:6292-6300.

Levesque et al., (2006), "Association between immunogenicity and adsorption of a recombinant *Streptococcus pneumoniae* vaccine antigen by an aluminum adjuvant," Hum Vaccin., 2(2):74-7.

Li et al., (2008), "IL-21-mediated Foxp3 suppression leads to enhanced generation of antigen-specific CD8+ T lymphocytes," Blood, 111:229-235.

Lindblad, (2004), "Aluminium compound for use in vaccines," Immunol Cell Biol., 82:497-505.

Lord et al., (2007), "Low dose metronomic oral cyclophosphamide for hormone resistant prostate cancer: a phase II study," J. Urology, 177:2136-2140.

Lu et al., (2002), "Rcognition of prostate tumor cells by cytotoxic T lymphocytes specific for prostate-specific membrane antigen," Cancer Res., 62:5807-5812.

Lubaroff et al., (2006), "Decreased cytotoxic T cell activity generated by co-administration of PSA vaccine and CpG ODN is associated with increased tumor protection in a mouse model of prostate cancer," Vaccine, 24:6155-6162.

Mantovani et al., (2003), "Reconstructive Urethroplasty using porcine acellular matrix," Eur. Urol., 44:600-602.

Martin, (1997), "Development of an adjuvant to enhance the immune response to influenza vaccine in the elderly," Biologicals, 25(2):209-131.

Matrisian et al., (2001), "Epithelial-stromal interactions and tumor progression: meeting summary and future directions," Cancer Res., 61:3844-3846.

Matsueda et al., (2005), "Identification of peptide vaccine candidates for prostate cancer patients with HLS-A3 super-type alleles," Clin. Cancer Res., 11:6933-6943.

McDevitt et al., (2003), "Transforming growth factor-B1 in a sterilized tissue derived from the pig small intestine submucosa," J. Biomed. Mater. Res., 67A:637-640.

McNeel et al., (2001), "Identification of T helper epitopes from prostatic acid phosphatae," Cancer Res., 61:5161-5167.

Mendez et al., (2003), "Coinjection with CpG-containing immunostimulatory oligodeoxynucleotides reduces the pathogenicity of a live vaccine against cutaneous Leishmaniasis but maintains its potency and durability," Infect Immun. 71(9):5121-9.

Michael et al., (2005), "Delayed disease progression after allogeneic cell vaccination in hormone-resistant prostate cancer and correlation with immunologic variables," Clin. Cancer Res., 11:4469-4478.

Miller et al., (2006), "The role of melatonin in immuno-enhancement: potential application in cancer," Int. J. Exp. Path., 87:81-87.

Moody et al., (1994), "Interleukin-2 transfected prostate cancer cells generate a local antitumor effect in vivo," Prostate, 24:244-251.

Moschella et al., (2003), "Shifting gene expression profiles during ex vivo culture of renal tumor cells: implications for cancer immunotherapy," Oncology Res., 14:133-145.

Mosolitis et al., (2005), "Towards therapeutic vaccines for colorectal carcinoma: a review of clinical trials," Expert Rev. Vaccines, 4:329-350.

Mullen et al., (2006), "Enhancement of functional antibody responses to AMA1-C1/Alhydrogel, a *Plasmodium falciparum* malaria vaccine, with CpG oligodeoxynucleotide," Vaccine, 24(14):2497-505.

Nomura et al., (2000), "Serum selenium and subsequence risk of prostate cancer," Cancer Epidemiology, Biomarkers & Prevention, 9:883-887.

Ochsenbein et al., (1999), "Immune surveillance against a solid tumor fails because of immunological ignorance," Proc. Natl. Acad. Sci. USA, 96:2233-2238.

O'Connor et al., (2001), "Successful repair of uretero-neobladder structure using porcine small intestine submucosa," J. Urology, 165:1995.

O'Connor et al., (2002), "Distal ureteral replacement with tubularized porcine small intestine submucosa," Urology, 60:697x-697xii.

O'Connor et al., (2002), "Novel modification of partial nephrectomy technique using porcine small intestine submucosa," Urology, 60:906-909.

Ohashi et al., (2000), "Significance of tumor associate eosinophilia and other inflammatory cell infiltrate in early esophageal squamous cell carcinoma," Anticancer Res., 20:3025-3030.

Okaji et al., (2004), "Vaccination with autologous endothelium inhibits angiogenesis and metastasis of colon cancer through autoimmunity," Cancer Science, 95:85-90.

Ou et al., (2008), "Enhancement of dendritic cell-tumor fusion vaccine potency by indoleamine-pyrrole 2,3-dioxygenase inhibitor, 1-MT," J. Cancer Res. Clin Oncol., 134:525-533.

Palese, (2006), "Making better influenza virus vaccines?" Emerg Infect Dis., 12(1):61-5.

Paradiso et al., (2003), "Plaque surgery for Peyronie's disease: heterologous grafts," Archivio Italiano di Urologia e Andrologia, 75:116-118 (Italian language with English abstract).

Peng et al., (2006), "Novel vaccines for the treatment of chronic HBV infection based on mycobacterial heat shock protein 70," Vaccin, 24(7):887-96.

Peretz et al., (2001), "Antibodies inhibit prion propagation and clear cell cultures of prion infectivity," Nature, 412(6848):739-43.

Peters et al., (1979), "Preparation of immunotherapeutic autologous tumor cell vaccines from solid tumors," Cancer Res., 39:1353-1360.

Petrik et al., (2007), "Aluminum adjuvant linked to Gulf War illness induces motor neuron death in mice," Neuromolecular Med., 9:83-100.

Petrovsky, (2006), "Novel human polysaccharide adjuvants with dual Th1 and Th2 potentiating activity," Vaccine, 24S2:S2/26-S2/29.

Pilla et al., (2006), "A phase II trial of vaccination with autologous, tumor-derived heat-shocked protein peptide complexes Gp96, in combination with GM-CSF and interferon-a in metastatic melanoma patients," Cancer Immunol Immunother., 55:958-968.

Pimenta et al., (2006), "Intranasal immunization with the cholera toxin B subunit-pneumococcal surface antigen A fusion protein induces protection against colonization with *Streptococcus pneumoniae* and has negligible impact on the nasopharyngeal and oral microbiota of mice," Infect Immun., 74(8):4939-44.

Pollard et al., (1975), "Transplantable metastasizing prostate adenocarcinomas in rats," J. Natl. Cancer Inst., 54:643-649.

Pollard et al., (1986), "Production of autochthonous prostate cancer in Lobund-Wistar rats by treatments with N-Nitroso-N-methylurea and testosterone," J. Natl. Cancer Inst., 77:583-587.

Pollard et al., (1987), "Autochthonous prostate cancer in Lobund-Wistar rats; a model system," The Prostate, 11:219-227.

Pollard et al., (2005), "Hormone-refractory prostate cancer in the Lobund-Wister rat," Exp. Biol. Med., 230:520-526.

Pollard et al., (2006), "Dietary prevention of hormone refractory prostate cancer in Lobund-Wistar rats: a review of studies in relevant animal model," Comp. Med., 56:461-467.

Pollard, (1998), "Lobund-Wistar rat model of prostate cancer in man," The Prostate, 37:1-4.

Polymenidou et al., (2004), "Humoral immune response to native eukaryotic prion protein correlates with anti-prion protection," Proc Natl Acad Sci U S A,101 Suppl 2:14670-6.

Qin et al., (2004), "CpG ODN enhances immunization effects of hepatitis B vaccine in aged mice," Cell Mol Immunol., 1(2):148-52.

Rechsteiner et al., (2005), "Cutting edge: priming of CTL by transcutaneous peptide immunization with imiquimod," J. Immunol., 174:2476-2480.

Redfern et al., (2006), "Phase II trial of idiotype vaccination in previously treated patients with indolent non-Hodgkin's lymphoma resulting in durable clinical responses," J. Clin. Oncol., 24:3107-3112.

Ringler et al., (1985), "Protection of rabbits against experimental pasteurellosis by vaccination with a potassium thiocyanate extract of *Pasteurella multocida*," Infection & Immunity, 49:498-504.

(56) References Cited

OTHER PUBLICATIONS

Rosado-Vallado et al., (2005), "Aluminium phosphate potentiates the efficacy of DNA vaccines against *Leishmania mexicana*," Vaccine, 23(46-47):5372-9.
Rosset et al., (2004), "Breaking immune tolerance to the prion protein using prion protein peptides plus oligodeoxynucleotide-CpG in mice," J Immunol., 172(9):5168-74.
Rousseau et al., (2006), "Immunotherapy of high-risk acute leukemia with a recipient (autologous) vaccine expressing transgenic human CD40L and IL-2 after chemotherapy and allogeneic stem cell transplantation," Blood, 107:1332-1341.
Ruozi et al., (2007), "Intact collagen and atelocollagen sponges: Characterization and ESEM observation," Mat. Sci. Eng., 27:802-810.
Sabirov et al., (2006), "Intranasal vaccination of neonatal mice with polysaccharide conjugate vaccine for protection against pneumococcal otitis media," Vaccine, 24(27-28):5584-92.
Sanderson et al., (1974), "The induction of tumour immunity in mice using glutaraldehyde-treated tumor cells," Nature, 248:690-691.
Schultz et al., (2002), "Porcine small intestine submucosa as a treatment for enterocutaneous fistulas," J. Am. Coll. Surg., 194:541-543.
Schwarz et al., (2004), "Immunisation with a synthetic prion protein-derived peptide prolongs survival times of mice orally exposed to the scrapie agent," Neurosci Left., 350(3):187-9.
Segura-Velázquez et al., (2006), "A novel synthetic adjuvant effectively enhances the immunogenicity of the influenza vaccine," Vaccine, 24(8):1073-80.
Sen et al., (2006), "Immunization of aged mice with a pneumococcal conjugate vaccine combined with an unmethylated CpG-containing oligodeoxynucleotide restores defective immunoglobulin G antipolysaccharide responses and specific CD4+-T-cell priming to young adult levels," Infect Immun., 74(4):2177-86.
Shekhar et al., (2001), "Breast stroma plays a dominant regulatory role in breast epithelial growth and differentiation: implications for tumor development and progression," Cancer Res., 61:1320-1326.
Sigurdsson et al., (2002), "Immunization delays the onset of prion disease in mice," Am J Pathol., 161(1):13-7.
Simons et al., (1999), "Induction of immunity to prostate cancer antigens: results of a clnical trial of vaccination with irradiated autologous prostate tumor cells engineered to secrete granulocyte-macrophage colony-stimulating factor using ex vivo gene transfer," Cancer Res., 59:5160-5168.
Simons et al., (2002), "Phase II trials of a GM-CSF genetransduced prostate cancer cell line vaccine (GVAX) in hormone refractory prostate cancer," Proc. Am. Soc. Clin. Oncol., 21:183a (Abstract 729).
Simons et al., (2006), "Granulocyte-macrophage colony-stimulating factor—transduced allogeneic cancer cellular immunotherapy: the GVAX® vaccine for prostate cancer," Urol. Oncol., 24:419-424.
Singh et al., (1992), "Stroma is critical for preventing or permitting immunological destruction of antigenic cancer cells," J. Exp. Med., 175:139-146.
Skountzou et al., (2006), "Transcutaneous immunization with inactivated influenza virus induces protective immune responses," Vaccine, 24:6110-6119.
Small et al., (2000), "Immunotherapy of hormone-refractory prostate cancer with antigen-loaded dendritic cells," J. Clin. Oncol., 18:3894-3903.
Small et al., (2005), "Results of a placebo-controlled phase III trial of immunotherapy with APC8015 for patients with homrone refractory prostate cancer (HRPC)," Proc. Am. Soc. Clin. Oncol., 23(16S):378S (Abstract 4500).
Souan et al., (2001), "Modulation of proteinase-K resistant prion protein by prion peptide immunization," Eur J Immunol, 31(8):2338-46.
Srinivasan et al., (2004), "Tumor antigens for cancer immunotherapy: therapeutic potential of xenogeneic DNA vaccines," J. Translational Med., 2:1-12.
Stack et al., (1982), "Autologous X-irradiated tumor cells and percutaneous BCG in operable lung cancer," Thorax, 37:599-593.
Stewart et al., (2006), "Pre-clinical evaluation of new adjuvant formulations to improve the immunogenicity of the malaria vaccine RTS,S/AS02A," Vaccine, 24(42-43):6483-92.

Suckow et al., (1991), "Heat-labile toxin-producing isolates of *Pasteurella multocida* from rabbits," Lab. Animal Sci., 41:151-156.
Suckow et al., (1999), "Enhanced bone regeneration using porcine small intestinal submucosa," J. Invest. Surg., 12:277-287.
Suckow et al., (2005), "Prevention of de novo prostate cancer by immunization with tumor-derived vaccines," Cancer Immunol Immunother., 54:571-576.
Suckow et al., (2005), "Use of porcine renal capsule matrix as a full-thickness dermal wound-healing material in rats," J. Wound Care, 14:137-140.
Suckow et al., (2007), "Prevention of human PC-346C prostate cancer growth in mice by xenogeneic tissue vaccine," Cancer Immunol. Immunother., 56:1275-1283.
Suckow et al., (2007), "Surgical Repair of Experimental Achilles Tenotomy with Porcine renal capsule material in a rat model," J. Mater. Sci. Mater. Med., 18:1105-1110.
Suckow et al., (2007), "Tissue vaccines for cancer," Expert. Rev. Vacc., 6:925-937.
Suckow et al., (2008), "Use of an extracellular matrix material as a vaccine carrier and adjuvant," Anticancer Res., 28(5A):2529-2534.
Sugai et al., (2005), "A CpG-containing oligodeoxynucleotide as an efficient adjuvant counterbalancing the Th1/Th2 immune response in diphtheria-tetanus-pertussis vaccine," Vaccine, 23(46-47):5450-6.
Süli et al., (2004), "Experimental squalene adjuvant. I. Preparation and testing of its effectiveness," Vaccine, 22(25-26):3464-9.
Sung et al., (2006), "HBV-ISS (Dynavax)," Curr Opin Mol Ther., 8(2):150-5.
Tatenhorst et al., (2005), "Genes associates with fast glioma cell migration in vitro and in vivo," Brain Pathol., 15:46-54.
Theeten et al., (2005), "Effects of lowering the aluminium content of a dTpa vaccine on its immunogenicity and reactogenicity when given as a booster to adolescents," Vaccine, 10;23(12):1515-21.
Tjoa et al., (1999), "Follow-up evaluation of a phase II prostate cancer vaccine trial," The Prostate, 40:125-129.
Tjoa et al., (2000), "Development of a dendritic cell-based prostate cancer vaccine," Immunology Letters, 74:873-893.
Totterman et al., (2005), "The immunotherapy of prostate and bladder cancer," B.J.U. Intl., 96:728-735.
Vermorken et al., (1999), "Active specific immunotherapy for stage II and stage III human colon cancer: a randomized trial," Lancet, 353:345-350.
Vieweg et al., (1994), "Immunotherapy of prostate cancer in the Dunning rate model: use of cytokine gene modified tumor vaccines," Cancer Res., 54:1760-1765.
Vitetta et al., (2006), "A pilot clinical trial of a recombinant ricin vaccine in normal humans," Proc Natl Acad Sci U S A, 103(7):2268-73.
Voytik-Harbin et al., (1998), "Small intestinal submucosa: a tissue-derived extracellular matrix that promotes tissue-specific growth and differentiation of cells in vitro," 4:157-174.
Wang et al., (1993), Lack of HLA class I antigen expression by melanoma cells SK-Mel-33 caused by reading a frameshift in β2-Microglobulin Messenger RHNA,: J. Clin. Invest., 91:648-692.
Wei et al., (2002), "Immunotherapy of tumors with vaccines based on xenogeneic homologous molecules," Anti-Cancer Drugs, 13:229-235.
Wei et al., (2006), "Dendritoma vaccination combined with low dose interleukin-2 in metastatic melanoma patients induced immunological and clinical responses," Intl. J. Oncol., 28:585-593.
Weiser et al., (2003), "Single layered small intestinal submucosa in the repair of sever chordee and complicated hypospadias," J. Urology, 170:1593-1595.
Wilson et al., (1997), "Human prostate tumor angiogenesis in nude mice: metalloprotease and plasminogen activator activities during tumor growth and neovascularization of subcutaneously injected matrigel impregnated with human prostate tumor cells," Anatomical Record, 249:63-73.
Xue et al., (1997), "Induction of human cytotoxic T lymphocytes specific for prostate-specific antigen," Prostate, 30:73-78.
Zhang et al., (2003), "Dendritic cells transfected with interleukin-12 and pulsed with tumor extract inhibit growth of murine prostatic carcinoma in vivo," Prostate, 55:292-298.

\* cited by examiner

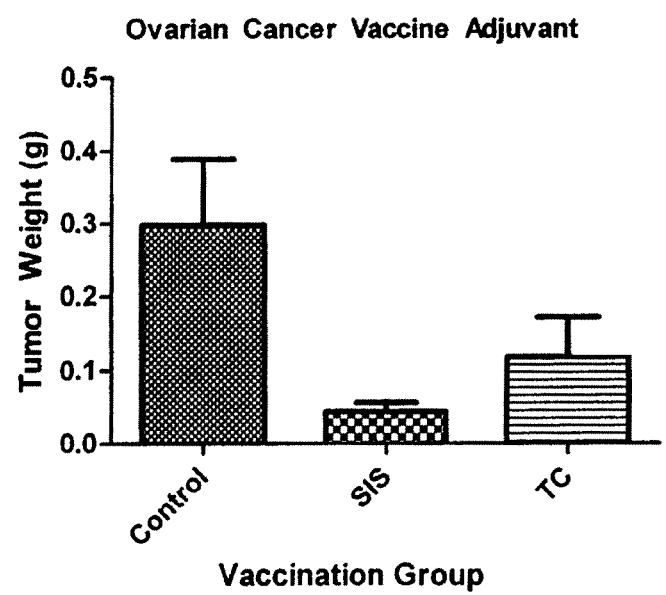

EXTRACELLULAR MATRIX ADJUVANT AND METHODS FOR PREVENTION AND/OR INHIBITION OF OVARIAN TUMORS AND OVARIAN CANCER

STATEMENT OF JOINT RESEARCH AGREEMENT

In compliance with 37 C.F.R. §1.71(g)(1), disclosure is herein made that the claimed invention was made pursuant to a Joint Research Agreement as defined in 35 U.S.C. §103© (3), that was in effect on or before the date the claimed invention was made, as a result of activities undertaken within the scope of the Joint Research Agreement, by or on the behalf of the University of Notre Dame and Cook Biotech, Inc. (West Lafayette, Ind.).

BACKGROUND

1. Field of the Invention

The present invention relates to the field of tissue specific types of pharmaceutical adjuvants, and in particular, vaccine adjuvants that may be used in preparations for the treatment and/or inhibition of ovarian tumors and/or ovarian cancers. The present invention also relates to the field of ovarian cancer vaccine preparations, as the adjuvants may be provided as part of a pharmaceutical composition for the treatment of ovarian cancer, such as in an ovarian cancer vaccine. The present invention also relates to methods for treating an animal, and human patients, for ovarian cancer, and methods for preventing and/or inhibiting ovarian cancer in an animal and in a human patient, and for inhibiting the growth of an ovarian tumor. In particular, the invention also relates to the filed of immunization methods, as a method for immunizing an animal, and a human patient, for ovarian cancer is provided. In particular, the invention provides preparations, such as vaccine preparations, that include the pharmaceutical adjuvant, specifically an ovarian cancer vaccine adjuvant, together with an ovarian tumor antigen and/or antigens as part of an immunization regimen to immunize an animal for ovarian cancer.

2. Related Art

Human ovarian cancer is a common gynecological malignancy. Ovarian cancers shed cells into the naturally occurring fluid within the abdominal cavity. These cells can implant on other abdominal (peritoneal) structures, including the uterus, urinary bladder, bowel and the lining of the bowel wall (omentum).

Stage I ovarian cancers are confined to one or both ovaries. In Stage II, the ovarian cancer has spread to pelvic but not the abdominal organs. In Stage III, the ovarian cancer has spread to abdominal organs and in Stage IV, the cancer has spread to distant sites, for example the lung, brain, or lymph nodes in the neck. Within these stages there are subcategories that are identified based on tumor size, node involvement and metastatic status. Thus a tumor can be a IIA, which describes a tumor that has spread and attached to the uterus, where as a IIB tumor describes a tumor that has in addition spread to other pelvic tissues, but with no cancer cells in the ascites or peritoneum, and so on. In addition to tumor staging, ovarian tumors, a type of epithelial tumor, can also be graded. Grade refers to the character of the cells of the tumor. Grade 1 is the least malignant with well-differentiated cells, Grade 2 is intermediate with moderately differentiated cells, and Grade 3 is the most malignant with poorly differentiated cells.

Ovarian cancer generally has a poor prognosis. It is estimated that one woman in 100 will die from this cancer in the United States. Ovarian cancer is disproportionately deadly because it lacks any clear early detection or screening test, meaning that most cases are not diagnosed until they have reached advanced stages. For example, more than 60% of patients presenting with this cancer already have Stage III or Stage IV ovarian cancer. The five-year survival rate for all stages of ovarian cancer is only 45.5%. Because of its aggressive nature, new approaches to the prevention and/or treatment of ovarian cancer are needed.

SUMMARY

The present invention, in a general and overall sense, relates to a uniquely effective and robust ovarian cancer adjuvant composition identified by the inventors to significantly enhance the anti-tumor activity of a preparation against the growth of an ovarian tumor, and in particular, against ovarian cancer in an animal, particularly, a human patient.

In some embodiments, the invention provides an adjuvant composition suitable for use as an adjuvant for an ovarian tumor and/or ovarian cancer vaccine. For example, the ovarian tumor/cancer adjuvant may be used in combination with an ovarian tumor antigen or antigens, such as an ovarian tissue preparation (inactivated, non-viable, non-replicative ovarian tumor/cancer tissue), to provide a preparation that enhances the immunizing, protective, anti-ovarian tumor physiological benefit to an animal and/or patient being treated for ovarian cancer and/or an ovarian tumor. By way of example, and in some embodiments, the adjuvant may be further described as comprising an extracellular matrix (ECM) adjuvant, together with an inactivated ovarian tumor/cancer tissue as antigen. The inactivated, non-viable ovarian tumor tissue is prepared by processing the ovarian tumor tissue in such as way that the ovarian tumor tissue is no longer able to give rise to ovarian tumor/cancer cells and/or tumor growth associated with ovarian tumors or ovarian cancers.

As used in the description of the present invention, the ovarian tumor tissue of the compositions as part of a vaccine or other immuno-protective preparation is described as non-viable, that is, a preparation comprised of ovarian tumor tissue that is unable to replicate and/or give rise to other ovarian tumor cells or tissue under normal, physiologically supportive conditions. For example, normal, physiologically supportive conditions may be described as under ordinary mammalian cell culture conditions or when placed and/or injected into an animal/human. An ovarian tumor tissue may be rendered non-viable according to many techniques, including radiation treatment, chemical lysis, ultrasound lysis, freezing, freeze-drying, chemical processing (glutaraldehdye, etc), exposure to particular heating temperatures, or other techniques known to those of skill in the art. Thus, the preparations and compositions that include the ovarian tumor adjuvant when administered together with the ovarian tumor antigen and/or antigens would not be expected to be capable of giving rise to or creating an ovarian tumor and/or ovarian tumor growth in the animal.

As used in the description of the present invention, an ovarian cancer and/or tumor vaccine relates to a preparation and/or composition that comprises a variant or derivative of an antigen or antigens of an ovarian tumor and/or ovarian cancer tissue, that when presented in a composition with the ovarian tumor adjuvant, will result in an immunologically detectable protective or immune response against ovarian tumor growth and/or ovarian cancer in an animal, such as in a human patient. Thus, and according to some embodiments of the invention, the ovarian cancer preparations and/or vaccines disclosed herein provide variants or derivatives of ovarian cancer cells that are presented to the body in order to induce an immune response against ovarian cancer cells. The induced response allows the immune system to attack, kill and remove ovarian cancer cells resulting in the prevention and/or treatment of ovarian cancer and/or ovarian tumor growth.

As used in the description of the present invention, an adjuvant relates to a substance which enhances the immune response to an ovarian tumor and/or ovarian cancer immunogenic species (antigen or combination of antigens), such as an ovarian tumor tissue or ovarian cancer tissue.

According to some embodiments, the invention provides a composition suitable for use as an ovarian cancer vaccine comprising an immunogenic amount of a non-viable ovarian cancer antigen preparation, and an extracellular matrix (ECM) adjuvant, wherein the immunogenic amount of the non-viable ovarian cancer antigen preparation in the presence of the ovarian cancer vaccine adjuvant is less than the immunogenic amount of the ovarian cancer antigen preparation sufficient to stimulate a protective response in the absence of the adjuvant.

In some embodiments, the ovarian cancer antigen preparation of the ovarian tumor and/or ovarian cancer tissue comprises human ovarian cancer and/or tumor tissue cells. In some embodiments, the human ovarian cancer and/or tumor cells may be described as non-viable human ovarian cells, and/or inactivated human ovarian cancer cells. In yet other embodiments, the ovarian cancer vaccine adjuvant comprises an extracellular matrix tissue, such as small intestinal mucosal tissue (SIS), or urinary bladder extracellular matrix tissue.

In some specific embodiments, the compositions of the present invention relate to an ovarian tumor inhibiting preparation comprising an ovarian tissue adjuvant (such as an extracellular matrix tissue) and non-viable (inactivated) ovarian cancer tissue cells.

In other embodiments, the ovarian tissue adjuvant comprises an extracellular matrix tissue that is renal capsule tissue, small intestinal submucosal tissue or fascial extracellular matrix tissue.

Embodiments disclosed herein also include methods of preparation for the ovarian cancer vaccine. In some embodiments, the method comprises combining an ovarian tissue adjuvant comprising an extracellular matrix tissue with an immunogenic amount of an ovarian cancer antigen (such as ovarian tumor tissue, ovarian cancer tissue and/or ovarian tumor cells that are non-viable (i.e., non-proliferating)).

According to yet other embodiments, a method for inhibiting ovarian tumor growth and/or treating or inhibiting ovarian cancer in an animal is provided. In some embodiments, the method may be described as comprising administering an immunogenic amount of a composition comprising non-viable ovarian cancer antigen and/or non-viable ovarian tumor cells and an ovarian tissue adjuvant sufficient to stimulate an anti-ovarian tumor response in the animal, wherein the anti-ovarian tumor response is enhanced 2-fold compared to anti-ovarian tumor response in the absence of the ovarian tissue adjuvant. In some embodiments, the anti-ovarian tumor response is enhanced about 63% compared to anti-ovarian tumor response in the absence of the ovarian tissue adjuvant.

In some embodiments, the non-viable ovarian tumor cell preparation comprises an inactivated, non-proliferating preparation of ovarian tumor tissue and/or ovarian tumor tissue cells. In even further embodiments, the non-viable ovarian tumor tissue cell preparation is described as other than a purified, single cell line cultured preparation of ovarian tumor cells. It is envisioned that the antigenic heterogeneity of the ovarian tumor and/or ovarian cancer cell preparation of the present invention provides at least in part the significantly enhanced immunogenicity of the present preparations as effective against ovarian cancer and ovarian tumor growth in an animal.

In yet other embodiments, a method for inhibiting growth of an ovarian tumor in an animal is provided. In some embodiments, the method comprises administering to an animal having an ovarian tumor the composition disclosed herein. In another embodiment, the growth of the ovarian tumor is inhibited 2-fold or more, relative to the ovarian tumor growth inhibition observed in an animal having been treated with a composition of non-viable ovarian tumor and/or non-viable ovarian cancer cells without the ovarian tissue adjuvant (extracellular matrix tissue, SIS) disclosed herein ( ).

In yet another embodiment, an implantable preparation is provided. In some embodiments, the implantable preparation comprises extracellular matrix tissue and a non-viable ovarian tumor tissue and/or non-viable ovarian cancer cells. In some embodiments, the implantable preparation is further defined as comprising a sheet of an extracellular matrix tissue, such as a sheet of small intestinal submucosal tissue (also called SIS, a strong pliable tissue taken from porcine intestine (Cook Biotech, 1425 Innovation Place, West Lafayette, Ind., 47906 USA)). In yet another embodiment, the implantable preparation is further defined as a gel or as a particulate preparation of an extracellular matrix material.

In yet other embodiments, an ovarian cancer vaccine comprising an extracellular matrix material adjuvant and a preparation of non-viable ovarian tumor tissue and or ovarian cancer cells, is provided. In some embodiments, the non-viable ovarian tumor cells or non-viable ovarian cancer tissue is human ovarian tumor cells or human ovarian cancer tissue.

The following abbreviations are used throughout the description of the present invention:
ECM—Extracellular Matrix;
FEM—Fascia Extracellular Matrix Material;
GFT—Glutaraldehyde Fixed Tumor;
LW Rat—Lobund-Wistar rat;
MEM—Modified Eagle's Medium;
PAIII—Prostate Adenocarcinoma III Cell Line from LW rats;
RCM—Renal Capsule Material;
SIS—Small Intestinal Submucosa;

BRIEF DESCRIPTION OF THE DRAWINGS

FIG. 1, according to some embodiments of the invention, demonstrates the inhibition of tumor cell growth through use of the extracellular matrix (ECM) as an adjuvant. (Control=Media only; SIS (included approximately $5 \times 10^6$ ES-2 cells per section of SIS); TC—glutaraldehdye—fixed—tumor cells. Addition of the ECM adjuvant (SIS) to the vaccine resulted in a 63% decrease in tumor growth, thus demonstrating the enhanced anti-tumor response by ECM adjuvant.

DETAILED DESCRIPTION

Definitions

The term "adjuvant" is defined as a substance which enhances the immune response to an immunogen, relative to the immune response to the immunogen without the adjuvant.

The term "adjuvancy" is defined as the ability of an agent to enhance and/or promote the immune response of an animal to a particular immunogen.

The term "biosynthetic material" is defined as a material that is in part or whole made up from or derived from a biological tissue.

The term "biological tissue" is defined as an animal tissue, including human or non-human tissue that is or that once was (cadaver tissue, for example) part of a living tissue or organism.

The term "extracellular matrix" (hereinafter "ECM") is defined as a tissue derived or bio-synthetic material that is capable of supporting the growth of a cell or culture of cells. By way of non-limiting examples, some particular ECMs include small intestinal submucosa (SIS), renal capsule material (RCM), facial extracellular matrix (FEM) and/or urinary bladder extracellular matrix tissue.

The term "FEM" relates to ECM derived from the fascia of porcine or other sources.

The term "immunize" is defined as eliciting an immune response in an animal, both a humoral immune response and a cellular immune response.

The term "immune provoking amount" is defined as an amount of the antigen required to elicit an immune response in the animal.

The term "non-viable" is intended to define cells or tissues, such as ovarian tumor tissue or ovarian cancer tissue, that is unable to replicate and/or give rise to other ovarian tumor cells or tissue under normal, physiologically supportive conditions. For example, normal, physiologically supportive conditions may be described as under ordinary mammalian cell culture conditions or when placed and/or injected into an animal/human. A tissue may be rendered non-viable by treatment or processing according to many different techniques, including radiation treatment, freezing, freeze-drying, chemical processing (glutaraldehdye, etc), exposure to particular heating temperatures, or other techniques.

The term "RCM" relates to ECM derived from the renal capsule of porcine or other sources.

The term "stroma" refers to a whole cell mixture comprising animal (human or non-human) supportive or connective tissue characteristic of that tissue located in or around a tissue or organ, particularly that connective and/or supportive tissue located in or around a tumor tissue or whole tumor as found in vivo, i.e., in the body. Stromal preparations may not be characterized by a single type or species of cells or proteins. For example, they can be instead characterized by a mixture of diverse antigenic species characteristic of a whole stromal tissue preparation as observed in vivo in association with a whole organ or tumor.

The term "tissue preparation" refers to a heterologous mixture of tumor cell and non-tumor cell tissue. The non-tumor cell tissue can comprise, for example, connective tissue, stroma, blood, serum, bone cells, blood, vessels, or any other animal (human or non-human) cell other than tumor cells. The tissue preparation comprises a diverse mixture of defined and undefined antigenic species, and is comprised of antigens present on the surface and inside of whole tumor and associated (connective tissue) non-tumor cells, in a disrupted or intact cell form. A tissue vaccine of embodiments disclosed herein can include whole cells, cell lysates, tissue preparations that include tumor tissue and other tissues, such as connective and supporting tissues (stroma), etc. The term is not intended to be defined as an isolated cellular component or protein, or finite number of strictly enumerated antigenic species characteristic of a tumor cell or a connective tissue alone. Hence, as used herein, the tissue preparation and vaccines prepared there from or method of using employing them presents numerous targets (antigenic species) that induce an immunogenic response to a multiplicity of tumor tissue and connective tissue antigenic species. A broad spectrum antigenic immune response can thus be elicited in an animal (human or non-human) vaccinated with the tissue preparations, and can provide the anti-tumor activity described herein.

The term "tumor" refers to a combination of neoplastic tissue and associated supporting stroma and connective tissue.

The terms "vaccine" and "cancer vaccine" are defined as any preparation capable of being used as an inoculation material or as part of an inoculation material, that will provide a treatment for, inhibit and/or convey immunity to cancer and/or tumor growth.

The term "xenogeneic" refers to a tissue or other material that is obtained from a source that is distinct from another, such as not having been obtained from the same species of animal (human vs. mouse), or same type of animal tissue (heart vs. lung).

The presently described compositions and methods provide anti-cancer and anti-tumor vaccines that prevent and/or inhibit ovarian cancer and tumor growth in vivo. In general, cancer vaccines have been administered without an adjuvant or with specific cytokines included as adjuvants.

Vaccinations

The present multivalent ovarian cancer vaccines capture the greatest range of relevant antigens, and therefore are of significant clinical utility. In this regard, the ovarian tissue vaccines of embodiments disclosed herein are made of harvested ovarian tumor material, and as such, are composed of a rich antigenic menu. In addition, the ovarian tissue vaccine adjuvants and vaccines that include them together with ovarian cancer tissue and/or ovarian cancer cells as provided herein, are well tolerated by the animal/patient in vivo.

The ovarian cancer tissue and/or ovarian tumor cell preparations can be described as processed preparations in which a heterologous mixture of ovarian tumor antigenic species characteristic of intact ovarian tumor tissue and surrounding connective and stromal tissue has been preserved. In some embodiments, the processed ovarian tissue preparation comprises a whole ovarian tumor tissue and connective (stromal) tissue sample that has been chemically treated to render it non-viable, such as by treatment with glutaraldehdye-(GFT), potassium thiocyanate (PTE), or other chemical or other technique as described herein, as recognized by those of skill in the art. In addition, it is envisioned that the ovarian tumor and/or ovarian cancer preparation used as part of the herein described ovarian cancer vaccines may be provided by the use of an ovarian tumor and or ovarian cancer tissue cell line that is non-viable.

Without being bound by theory, it is believed that xenogeneic vaccines such as the ones described herein may allow the immune system to overcome tolerance to self-antigens expressed by tumors, thus stimulating a vigorous immunity to homologous antigens. In this way, xenogeneic vaccines may have an advantage over autologous or even allogeneic vaccines. The vaccine preparations are mixtures which contain a variety of potent antigens. In the case of prevention, the immune systems of vaccinated animals can rapidly respond to preneoplastic lesions and effectively target occasional cancer cells as they develop. In the case of treatment, the immune system faces the much greater challenge of targeting an enormous number of active cells which can induce immune tolerance and quickly alter phenotype to adapt to selective pressures from treatment. The vaccines also include connective tissue components which are not neoplastic but which can be altered by cytokine or other signals from the neoplastic cells to organize needed connective tissue and stromal infrastructure for tumor support, growth and progression. Because these connective tissue components are not neoplastic, they cannot alter their immunophenotype as easily as neoplastic cells in order to evade an immune response resulting from vaccination with a vaccine directed against these components. In this way, then, vaccination against tumor connective tissue and stromal components allows a protective immune response that the tumor cannot escape by rapidly altering immunophenotype, an escape mechanism commonly employed by neoplastic cells.

Ovarian Cancer Vaccine Adjuvant

SIS is a commercially available accellular extracellular matrix (ECM) preparation produced from porcine small intestinal submucosa. SIS is a naturally derived, extracellular matrix, that is not synthetic or cross-linked. A commercial form of this collagenous acellular material is available from Cook Biotech, and is known by the trade name, "OASIS®". In this product, SIS is taken from a biological source and is processed to remove all cells. This product is biocompatible and safe for human use.

SIS has found substantial utility as a tissue growth scaffold. For example, SIS has shown wide utility in urology, wound care and repair, as an anal fistula plug, tendon repair, and bone healing. Following implantation, SIS rapidly attracts mononuclear inflammatory cells followed by ingrowth of host tissue. In this way, SIS serves as a scaffold for tissue repair. The SIS then becomes fully replaced by host tissue. Other extracellular matrices, such as porcine renal capsule material, behave in a similar fashion to SIS.

Accordingly, in one aspect, embodiments disclosed herein provide an extracellular matrix (ECM) material, such as a modified preparation of SIS, FEM, RCM, or other appropriate extracellular matrix material of choice, as an ovarian cancer vaccine adjuvant. In other embodiments, the ECM materials may be described as a modified preparation of SIS, FEM, RCM, or other extracellular matrix material of choice (diluted) about 2-fold to about 20-fold, or from about 5-fold to about 10-fold. In some embodiments, a standard SIS material, such as that obtained from a commercial vendor, is diluted about 1 to about 10 fold, and in this dilution, is particularly well suited for use as an injectable vaccine material.

In one aspect of embodiments disclosed herein, there is provided a composition comprising an immunogenically enhancing preparation of an extracellular matrix material, particularly the extracellular matrix of the small intestinal submucosa (SIS) or tissue of the renal capsule. In some embodiments, the extracellular matrix comprises a menu of antigenic species characteristic of porcine small intestinal mucosa. This preparation can also be described as comprising a small intestinal submucosa tissue preparation, or purified preparation thereof.

According to another aspect, there is provided a composition comprising an adjuvant and an ovarian cancer vaccine. In some embodiments, the ovarian cancer vaccine is a whole-ovarian cancer cell vaccine. In other embodiments, the ovarian cancer and/or tumor vaccine comprises an immunogenic amount of an ovarian tumor (non-viable); and an ovarian cancer and/or tumor adjuvant, wherein said ovarian cancer adjuvant comprises a preparation characteristic of an extracellular matrix material, and wherein the immunogenic amount of the ovarian cancer and/or tumor antigen preparation sufficient to stimulate an anti-ovarian cancer and/or tumor protective response in the presence of the adjuvant is less than the amount of the ovarian tumor antigen and/or ovarian cancer antigen sufficient to stimulate a protective response in the absence of the adjuvant.

Method of Preparing an Ovarian Cancer Vaccine Adjuvant

The present invention provides various methods for preparing an ovarian cancer vaccine adjuvant, as well as an ovarian cancer vaccine containing the ovarian cancer vaccine adjuvant. In some embodiments, the method comprises obtaining an amount of small intestinal submucosa (SIS) or other extracellular matrix material of choice (FEM, RCM), and preparing a processed preparation thereof suitable for use as an ovarian cancer vaccine adjuvant in combination with an immunogenic amount of an ovarian whole cell antigen, such as ovarian tumor and/or ovarian cancer cells. In particular, these ovarian tumor and/or ovarian cancer cells are treated so as to render them non-viable, such as by chemical treatment (glutaraldehdye) or other processing as described herein and as known in the art.

Method of Treating/Inhibiting/Immunizing an Animal Against Ovarian Cancer

According to yet another broad aspect, a method for treating and/or immunizing an animal having ovarian cancer or at risk of developing ovarian cancer is provided. Embodiments disclosed herein provide for both a human vaccine and an animal vaccine.

In some embodiments, the method for treating ovarian cancer employs a composition comprising a vaccine, the vaccine comprising an adjuvant composed of an extracellular matrix (ECM) material together with a tissue preparation, such as a glutaraldehyde-fixed xenogeneic tissue preparation of ovarian cancer cells and/or ovarian tumor cells. These preparations are found to be more immunogenic than use of the glutaraldehyde fixed xenogeneic tissue preparation without an extracellular matrix adjuvant.

Clinical Ovarian Cancer Treatment Preparations

In yet another aspect, embodiments disclosed herein provide a variety of unique clinical ovarian cancer treatment preparations. In some embodiments, these ovarian cancer treatment preparations can include as the adjuvant a gel, a sheet, particulate preparation or an injectable preparation of the extracellular matrix material as described herein. The injectable preparations may be further described as suitable for i.v. administration.

Combination Treatment Regimens and Preparations for Ovarian Cancer

In yet another aspect, embodiments disclosed herein provide a preparation and/or treatment regimen wherein the extracellular matrix (ECM) in its various forms as described herein, together with the ovarian cancer cell and/or ovarian tumor tissue as antigen, may be used in combination with another active agent, such as, without limitation, a T-cell suppressor (cyclophosphamide), cytokines, (IL-21), cytokine granulocyte/macrophage colony stimulating factor (GM-CSF), hormones (melatonin), immunosuppressive enzymes (1-methyl-tryptophane), COX-2 inhibitors (cyclooxygenase-2), oligonucleotides (CpG oligonucleotides), or any combination of these.

Customized Ovarian ECM Vaccines

In yet another aspect, embodiments disclosed herein provide a customized ovarian cancer ECM vaccine, where an intended patient's own ovarian tumor and/or ovarian cancer cell tissue/biopsy tissue is grown on an ECM material, such as SIS. Once the cells have had an opportunity to grow on the culture, the cells are either inactivated or removed, the ECM material washed, and then the ECM washed material is used together with a non-viable preparation of the patient's own ovarian cancer cells and or ovarian tumor tissue (as antigen), or alone without additional ovarian cancer or ovarian tumor tissue, as an ovarian cancer vaccine for the patient. This approach allows targeting of ovarian cancer tissue antigens which can be specific and unique to an individual patients' ovarian cancer and/or tumor. Further, embodiments disclosed herein allow expansion on an ECM of harvested ovarian cancer and/or ovarian tumor material to quantities that would be sufficient to provide ongoing booster vaccination as dictated by the clinical need of the patient.

Any non-toxic, inert and effective carriers can be used to formulate compositions of embodiments disclosed herein. Well known carriers used to formulate other therapeutic compounds for administration to humans particularly will be useful in the compositions of embodiments disclosed herein. Pharmaceutically acceptable carriers, excipients and diluents in this regard are well known to those of skill, such as those described in the MERCK INDEX, 11th Ed., Budavari et al., Eds., Merck & Co., Inc., Rahway, N.J. (1989), which is incorporated by reference herein in its entirety. Examples of such useful pharmaceutically acceptable excipients, carriers and diluents include, without limitation, distilled water, physiological saline, Ringer's solution, dextrose solution, Hank's solution and DMSO. Sterile formulations, such as those described in, without limitation, Mantile et al., J. Biol Chem. 268: 20343-20351 (1993), which is incorporated by reference herein for its teachings regarding the same, can also be used.

In further embodiments, the compositions and methods disclosed herein can be used in conjunction with additional treatments including, without limitation, surgical intervention, radiation therapy, hormonal therapy, immunotherapy, chemotherapy or cryotherapy.

Other embodiments of the invention will be apparent to those of skill in the art from consideration for the specification and practice of the invention disclosed herein. It is intended that the specification and examples be considered as exemplary only. The true scope and spirit of the invention may better be appreciated as set forth in the claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by embodiments disclosed herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

EXAMPLES

The present example sets forth the materials and methods employed in some of the embodiments of the invention, and as used throughout the description of the present invention.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

Example 1

Ovarian Cancer Inhibition In Vivo

The present example demonstrates the utility of the present invention for inhibiting the growth of ovarian tumors and for treating human ovarian cancer.

An ECM was evaluated for its ability to enhance the ability of a vaccine composed of inactivated ovarian cancer cells to inhibit growth of ovarian carcinoma tumors. It was demonstrated in a mouse model that the ECM adjuvant inhibited the growth of ovarian carcinoma by 63% over a vaccine composed of inactivated, cultured ovarian carcinoma cells. This result demonstrates that ECM is a powerful adjuvant for vaccines used to treat ovarian cancer.

In this study, a human ovarian carcinoma cell line (ES-2; American Type Culture Collection, Manassas, Va.) was used. In culture, the cells were grown in Dulbecco's Modified Eagle's Media with fetal bovine serum added to 10% concentration. SIS was obtained as a sterile, lyophilized sheet (Surgis®, Cook Biotech, Inc., West Lafayette, Ind.). The SIS was of porcine origin and was derived by removal of all mesenteric tissues, serosa, and tunica muscularis from segments of jejunum. Prior to culture with tumor cells, the SIS was cut into 2 cm×2 cm sections. ES-2 human ovarian carcinoma cells were grown in culture using Dulbecco's Modified Eagle's Medium with fetal bovine serum added to 10% concentration. Two vaccines were tested in this study: a control vaccine prepared by glutaraldehyde-fixation of cultured ES-2 cells (TC) and a vaccine prepared by glutaraldehyde-fixation of ES-2 cells grown on SIS in media with 10% FBS for seven days. Cells harvested from culture, either with or without SIS, were incubated in 2.5% glutarlaldehyde (v/v) at 37° C. for 2 hours and then washed thoroughly with media to produce the vaccine preparations. Four immunocompetent mice (Balb/C, 6-8 week old female; Harlan Laboratories, Inc.) per group were vaccinated once subcutaneously in the flank. One group was vaccinated with $5\times10^6$ glutaraldehyde-fixed ES-2 cells (TC vaccine) in a volume of 0.25 ml media. Four mice were similarly vaccinated with media only as a control. An additional group of four mice was anesthesized, prepared for aseptic surgery and implanted with a section of glutaraldehyde-fixed SIS with ES-2 cells. Based on an average number of cells found to grow in pilot studies on similar sections of SIS, it was reasoned that these sections contained approximately $5\times10^6$ ES-2 cells per section of SIS.

A boost of glutaraldehyde-fixed ES-2 cells (TC vaccine) was administered 7 days later. The glutaraldehyde-fixed SIS with ES-2 cells group did not receive a booster vaccine at day 7. Fourteen days after the first vaccination, mice were euthanized and their spleens aseptically harvested. The spleens were dissociated into medium using a screen and co-incubated for 3 hours at 37° C. with ES-2 cells (2:1 ratio of splenocytes to tumor cells). Groups of 8 syngenic, immunodeficient nude mice were then administered subcutaneously a suspension containing $1.5\times10^6$ mixed ES-2 cells and splenocytes from either SIS-vaccinated mice or controls; and 16 mice received ES-2 cells and splenocytes from mice vaccinated with TC. Mice were euthanized 21 days later and the tumors weighed. Results demonstrated that a significant ($p\leq0.05$) reduction in mean tumor weight was noted in mice receiving ES-2 cells mixed with splenocytes from mice vaccinated with the SIS vaccine, but not the TC vaccine, compared to mice receiving ES-2 cells mixed with splenocytes from mice vaccinated with media only.

What is claimed is:

1. A method for eliciting an immune response against ovarian cancer comprising administering a cellular preparation comprising non-viable ovarian tumor tissue and an ovarian tissue adjuvant to a patient in need thereof, wherein the non-viable ovarian tumor tissue comprises both ovarian tumor cells and non-tumor tissue, and wherein the ovarian tissue adjuvant is an extracellular matrix from a non-tumor tissue source.

2. The method of claim 1 wherein said tissue adjuvant comprises extracellular matrix derived from small intestinal submucosal tissue.

3. The method of claim 1 wherein the non-viable ovarian tumor tissue is processed with glutaraldehyde.

4. A method for inhibiting growth of an ovarian tumor in a patient in need thereof comprising administering a cellular preparation comprising non-viable ovarian tumor tissue and an ovarian tissue adjuvant to said patient, wherein the non-viable ovarian tumor tissue comprises both ovarian tumor cells and non-tumor tissue, and wherein the ovarian tissue adjuvant is an extracellular matrix from a non-tumor tissue source.

5. A method for inhibiting growth of an ovarian tumor in a patient in need thereof comprising administering a cellular preparation comprising non-viable ovarian tumor tissue and an ovarian tissue adjuvant to said patient, wherein the non-viable ovarian tumor tissue comprises both ovarian tumor cells and non-tumor tissue, wherein the ovarian tissue adjuvant is an extracellular matrix from a non-tumor tissue source and wherein the ovarian tumor tissue is xenogeneic.

6. A method for eliciting an immune response against ovarian cancer comprising administering a cellular preparation comprising non-viable ovarian tumor tissue and an ovarian tissue adjuvant to a patient in need thereof, wherein the non-viable ovarian tumor tissue comprises both ovarian tumor cells and non-tumor tissue, wherein the ovarian tissue adjuvant is an extracellular matrix from a non-tumor tissue source and wherein the ovarian tumor tissue is xenogeneic.

7. The method of claim 6 wherein the extracellular matrix is small intestinal submucosa.

8. A method for providing an enhanced ovarian tumor inhibiting preparation comprising combining non-viable ovarian tumor tissue with an ovarian tissue adjuvant, wherein the non-viable ovarian tumor tissue comprises both ovarian tumor cells and non-tumor tissue, and wherein the ovarian tissue adjuvant comprises a preparation characteristic of facial extracellular matrix or urinary bladder extracellular matrix.

9. An implantable preparation comprising an extracellular matrix adjuvant and non-viable ovarian tumor tissue, wherein the extracellular matrix adjuvant is from a non-tumor tissue source, and wherein the non-viable ovarian tumor tissue comprises both ovarian tumor cells and non-tumor tissue.

10. The implantable preparation of claim 9, wherein the extracellular matrix is further defined as a sheet, a gel or particulate preparation.

11. A non-human ovarian tissue preparation comprising non-viable, non-human ovarian tumor tissue and an extracellular matrix adjuvant, wherein the extracellular matrix is from a non-tumor tissue source, and wherein the non-human ovarian tumor tissue comprises both ovarian tumor cells and non-tumor tissue.

12. The non-human ovarian tissue preparation of claim 11 further comprising cyclophosphamide, a cytokine, granulocyte-macrophage colony stimulating factor, 1-methyl tryptophan, melatonin, CpG oligonucleotides, or combinations thereof.

13. An implantable preparation comprising an extracellular matrix adjuvant and human non-viable ovarian tumor tissue, wherein the extracellular matrix adjuvant is from a non-tumor tissue source, and wherein the non-viable ovarian tumor tissue comprises both ovarian tumor cells and non-tumor tissue.

14. The implantable preparation of claim 13, wherein the extracellular matrix adjuvant is small intestinal submucosa.

* * * * *